United States Patent
Epperson

(10) Patent No.: US 11,826,498 B2
(45) Date of Patent: *Nov. 28, 2023

(54) CAPSULE POD EXTERNAL FILTRATION SYSTEM

(71) Applicant: Derrack Epperson, Port Townsend, WA (US)

(72) Inventor: Derrack Epperson, Port Townsend, WA (US)

(*) Notice: Subject to any disclaimer, the term of this patent is extended or adjusted under 35 U.S.C. 154(b) by 392 days.

This patent is subject to a terminal disclaimer.

(21) Appl. No.: 16/898,334

(22) Filed: Jun. 10, 2020

(65) Prior Publication Data

US 2020/0297891 A1    Sep. 24, 2020

(51) Int. Cl.
| | |
|---|---|
| *A61L 9/20* | (2006.01) |
| *F24F 8/10* | (2021.01) |
| *E04H 1/12* | (2006.01) |
| *B01D 46/00* | (2022.01) |
| *A61G 10/02* | (2006.01) |
| *A61M 21/00* | (2006.01) |
| *A47C 21/04* | (2006.01) |
| *F24F 8/108* | (2021.01) |
| *F24F 8/22* | (2021.01) |

(52) U.S. Cl.
CPC ............. *A61L 9/20* (2013.01); *A47C 21/044* (2013.01); *A47C 21/046* (2013.01); *A61G 10/02* (2013.01); *A61M 21/0094* (2013.01); *B01D 46/0028* (2013.01); *F24F 8/108* (2021.01); *A61L 2209/12* (2013.01); *A61L 2209/14* (2013.01); *A61L 2209/16* (2013.01); *B01D 2279/35* (2013.01); *F24F 8/22* (2021.01)

(58) Field of Classification Search
CPC ............. A61L 9/20; F24F 8/10; E04H 1/1277
See application file for complete search history.

(56) References Cited

U.S. PATENT DOCUMENTS 2,184,484 A    12/1939  Bojner
3,505,989 A     4/1970  Truhan
(Continued)

FOREIGN PATENT DOCUMENTS

AU    2019100241 A4    4/2019
CN    103881350 A  *  6/2014
(Continued)

OTHER PUBLICATIONS

English Translation of CN 103881350 A provided by the European Patent Office website epacenet.com: Wang; Antimicrobial Polycarbonate Composite Plastic; Jun. 25, 2014 (Year: 2014).*

(Continued)

*Primary Examiner* — Kevin Joyner
(74) *Attorney, Agent, or Firm* — Davis Wright Tremaine LLP

(57) ABSTRACT

An external ventilation system of a capsule pod sleeping chamber that includes a wall with an exterior side that faces a communal space and an interior side that faces an interior of the capsule pod sleeping chamber. The external ventilation system further includes a duct to route first air out from the communal space to an area separated from air of the capsule pod sleeping chamber, where the duct is located between the exterior side and the interior side, and there is an aperture located on the exterior side opening into the duct.

11 Claims, 12 Drawing Sheets

(56) References Cited

U.S. PATENT DOCUMENTS

| | | | |
|---|---|---|---|
| 3,923,134 A | 12/1975 | Rezazadeh | |
| 4,535,684 A | 8/1985 | Perng | |
| 4,594,817 A | 6/1986 | McLaren et al. | |
| 5,009,685 A * | 4/1991 | Wilson | E04H 1/1277 55/467 |
| 5,487,240 A | 1/1996 | Miller | |
| 6,508,850 B1 | 1/2003 | Kotliar | |
| 7,251,953 B2 | 8/2007 | Wetzel et al. | |
| 7,707,931 B2 | 5/2010 | Garrett et al. | |
| 7,802,443 B2 | 9/2010 | Wetzel | |
| 10,039,681 B2 | 8/2018 | Ballantyne et al. | |
| 2004/0250481 A1 | 12/2004 | Frykman | |
| 2005/0050804 A1 | 3/2005 | Weidner | |
| 2006/0096198 A1 | 5/2006 | Kmet et al. | |
| 2006/0107635 A1 * | 5/2006 | Homan | A61G 10/023 55/385.2 |
| 2008/0120924 A1 | 5/2008 | Mintie et al. | |
| 2011/0160334 A1 | 6/2011 | Lisec | |
| 2017/0176034 A1 * | 6/2017 | Hussain | G05B 19/048 |
| 2018/0303691 A1 | 10/2018 | Heyerdahl et al. | |

FOREIGN PATENT DOCUMENTS

| | | |
|---|---|---|
| DE | 3603055 A1 | 8/1987 |
| KR | 200475651 Y1 | 12/2014 |
| KR | 20200102661 A | 9/2020 |
| KR | 102302890 B1 | 9/2021 |
| WO | 9509329 A1 | 4/1995 |
| WO | 9606314 A1 | 2/1996 |
| WO | 2018024209 A1 | 2/2018 |

OTHER PUBLICATIONS

International Search Report and Written Opinion dated Sep. 8, 2021, Patent Application No. PCT/US2021/036039, 17 pages.

* cited by examiner

US 11,826,498 B2

CAPSULE POD EXTERNAL FILTRATION SYSTEM

CROSS REFERENCE TO RELATED APPLICATION

This application incorporates by reference for all purposes the full disclosure of co-pending U.S. patent application Ser. No. 16/898,323, filed concurrently herewith, entitled "CAPSULE POD SLEEPING CHAMBER".

BACKGROUND

Field of the Invention

The present invention is directed generally to a capsule pod sleeping chamber.

Description of the Related Art

In modern times, a need often arises to provide accommodations to many people. For example, recent events have highlighted how susceptible humans are to large scale pandemics. Many victims of these infections end up in hospitals, often for weeks on end, which can quickly strain even the most ready and equipped areas as the number of patients overcome space in local hospitals. Even if space can be obtained, the risk of additional disease spread in the hospitals amongst care providers and other patients make additional cases of infection very likely. However, constructing new buildings can be time-consuming and expensive, and while converting existing building space to reasonably accommodate many people can present a quicker and cheaper option, this presents additional problems, such as an increased risk of communicable diseases spreading among people living in close quarters.

BRIEF DESCRIPTION OF THE SEVERAL VIEWS OF THE DRAWING(S)

Figure 11:
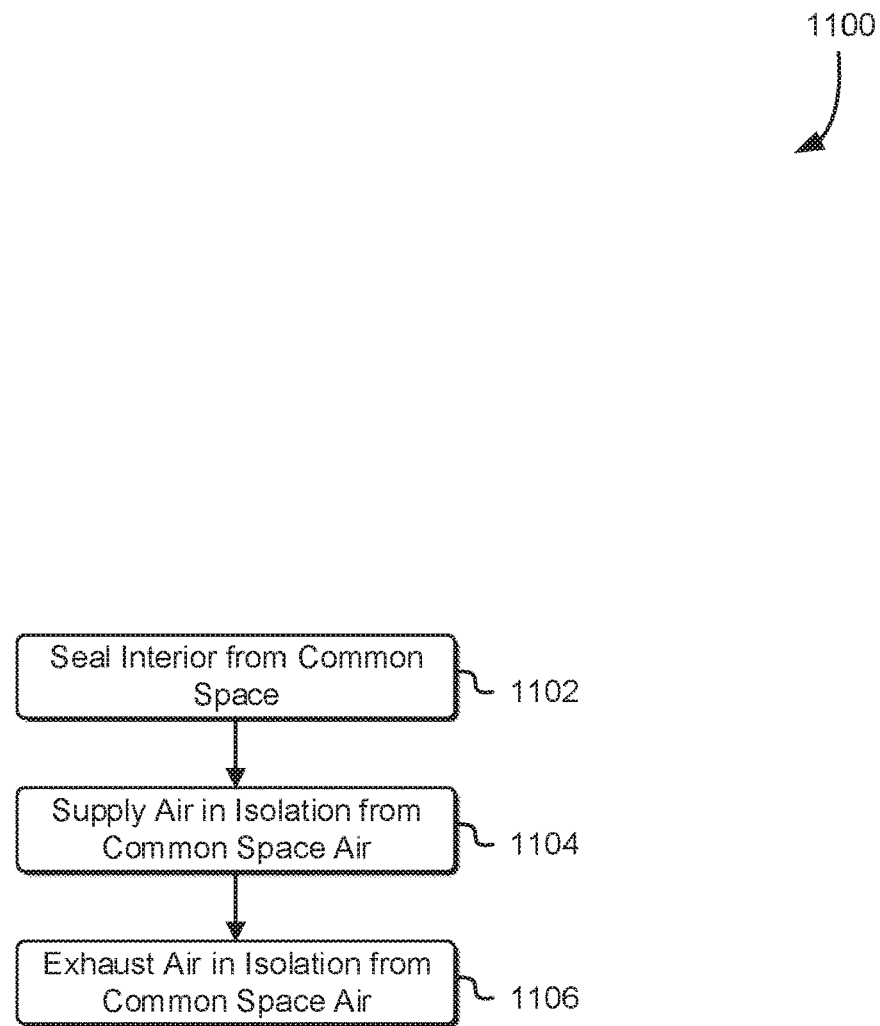
Figure 12:
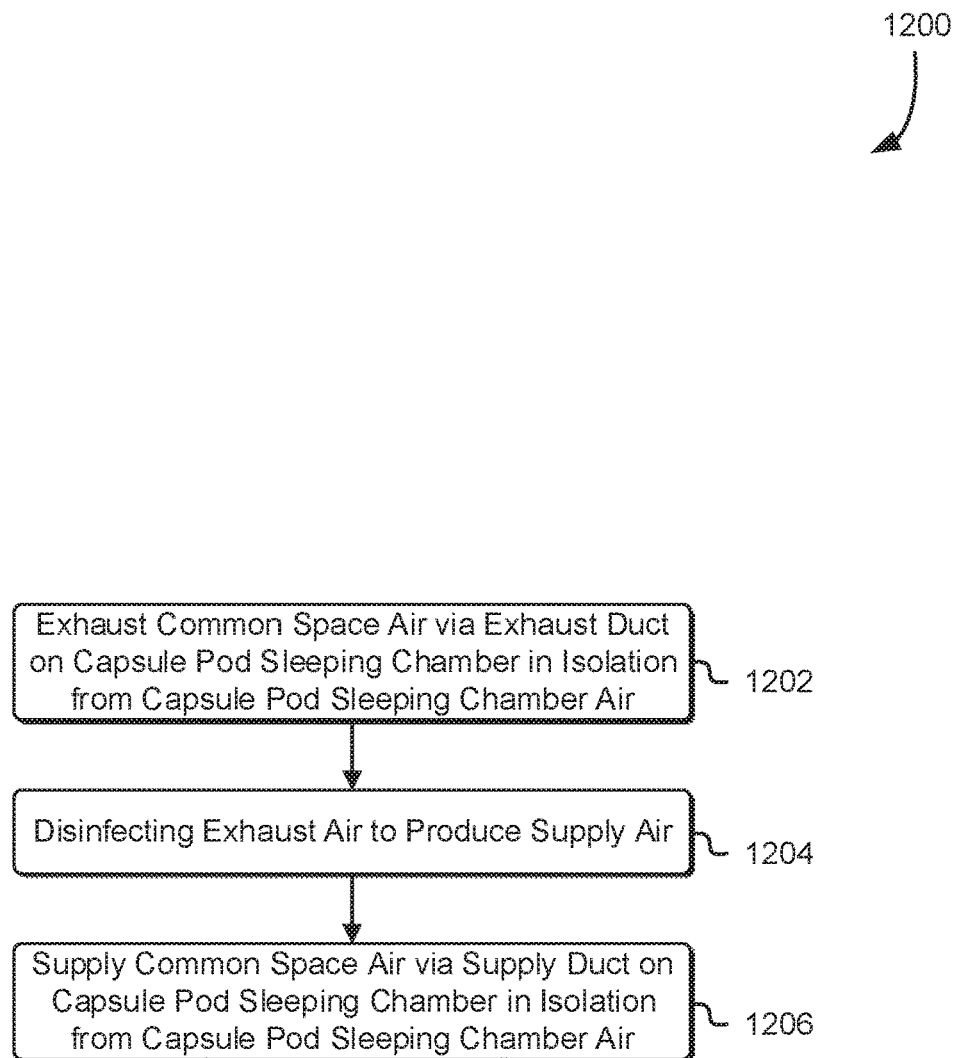

FIG. 11 is a flowchart that illustrates an example of clean air circulation for a capsule pod sleeping chamber located in a communal space in accordance with an embodiment of the present disclosure; and FIG. 12 is a flowchart that illustrates an example of clean air circulation in a communal space located in a vicinity of a capsule pod sleeping chamber in accordance with an embodiment of the present disclosure.

DETAILED DESCRIPTION OF THE INVENTION

Techniques and systems described below alleviate the disadvantages described above with the traditional types of capsule pod sleeping chambers. Benefits arising from the techniques and systems of the present disclosure include being able to quickly repurpose building space into clean, affordable, high-density housing. In this manner, the techniques and systems of the present disclosure can help alleviate issues arising from lack of affordable or available housing, such as homelessness, temporary shelter for disaster recovery victims, and hospital overcrowding.

Further benefits arising from the techniques and systems of the present disclosure include safeguarding the capsule pod sleeping chamber air from contamination by viruses, bacteria, dust, or other contaminants from the air in the common space where the capsule pod sleeping chamber is located. These benefits may be at least partially achieved by the capsule pod sleeping chamber having a separate ventilation system from the common space, whereby the air supplied to the capsule pod sleeping chamber may be provided as filtered and/or sterilized air. In this manner, the capsule pod sleeping chambers may be used to accommodate individuals who are at high risk for infection, such as elderly individuals, cancer patients, surgery patients, individuals in quarantine, or other individuals who may have deficient or compromised immune systems.

Still further benefits arising from the techniques and systems of the present disclosure include intercepting and filtering outside air in the immediate vicinity of the capsule pod sleeping chamber from viruses, bacteria, dust, or other contaminants. These benefits may be at least partially achieved by exterior vents on the capsule pod sleeping chamber that open into ducting that runs through one or more walls of the capsule pod sleeping chamber.

Hospitals and other medical facilities have a need to prevent communicable diseases from spreading to hospital staff or from patient to patient. Nursing homes may have elderly residents with weak immune systems. The capsule pod sleeping chambers described in the present disclosure may help protect individuals who are at high risk for infection, such as elderly individuals, cancer patients, surgery patients, individuals in quarantine, or other individuals who may have deficient or compromised immune systems by reducing viruses, bacteria, and other contaminants in the air from common areas, thereby reducing the chance of contaminated air from common areas entering an open capsule pod sleeping chamber and likewise reducing the chance of contaminated air from a capsule pod sleeping chamber mixing with air in the common space.

The capsule pod sleeping chambers of the present disclosure provide further benefit by increasing the capacity of building spaces to accommodate individuals. For example, a typical hospital room outfitted with two beds that hold one individual apiece may instead host six critical capsule pod sleeping chambers or eight non-critical capsule pod sleeping chambers, thereby tripling or quadrupling the capacity of the existing hospital room. In this manner, the productivity of hospital staff is also increased because the staff does not need to spend as much time going from room to room to visit patients. Likewise, a standard hotel room with one bed for two individuals may be instead configured with six non-critical capsule pod sleeping chamber to increase the capacity to six individuals. Similarly, homeless shelters may be transformed to utilize capsule pod sleeping chambers of the present disclosure to increase capacity and improve indoor air quality.

In some examples, a "non-critical capsule pod sleeping chamber" refers to a standard capsule pod sleeping chamber of the present disclosure as depicted in FIGS. 5-8 that abuts to one or more other capsule pod sleeping chambers. In contrast, a "critical capsule pod sleeping chamber" in some examples refers to a capsule pod sleeping chamber that is spaced apart from one or more adjacent capsule pod sleeping chambers so as to allow space for hospital equipment (e.g., heart monitors, oxygen tanks, intravenous drips) or to allow patients to be accessed from a left or right side capsule pod sleeping chamber door.

Still further, the benefits described above may be further facilitated by the modular design of the capsule pod sleeping chambers, which not only allow the capsule pod sleeping chambers to be laid out in rows and stacked, but the supply and exhaust ducts of each capsule pod sleeping chamber may be aligned so as to easily interconnect with supply and exhaust ducts of an adjacent capsule pod sleeping chamber.

A capsule pod sleeping chamber in some examples includes a ceiling and walls adjacent to the ceiling sealing an interior space to prevent a mixture of air between the interior space and a communal space exterior to the portable enclosure. In the examples, the capsule pod sleeping chamber has first duct to route supply air into the interior space from a first area that is separated from the communal space and a second duct to route exhaust air out from the interior space to a second area separated from the communal space. Lastly in the examples, the capsule pod sleeping chamber has a plurality of apertures located in at least one wall of the plurality of walls that include the first aperture opening into the first duct and the second aperture opening into the second duct.

An external ventilation system of a capsule pod sleeping chamber in some examples includes a wall with an exterior side that faces a communal space and an interior side that faces an interior of the capsule pod sleeping chamber. In the examples, the external ventilation system further includes a duct to route first air out from the communal space to an area separated from air of the capsule pod sleeping chamber, where the duct is located between the exterior side and the interior side (e.g., built-in), and there is an aperture located on the exterior side opening into the duct.

Figure 1:
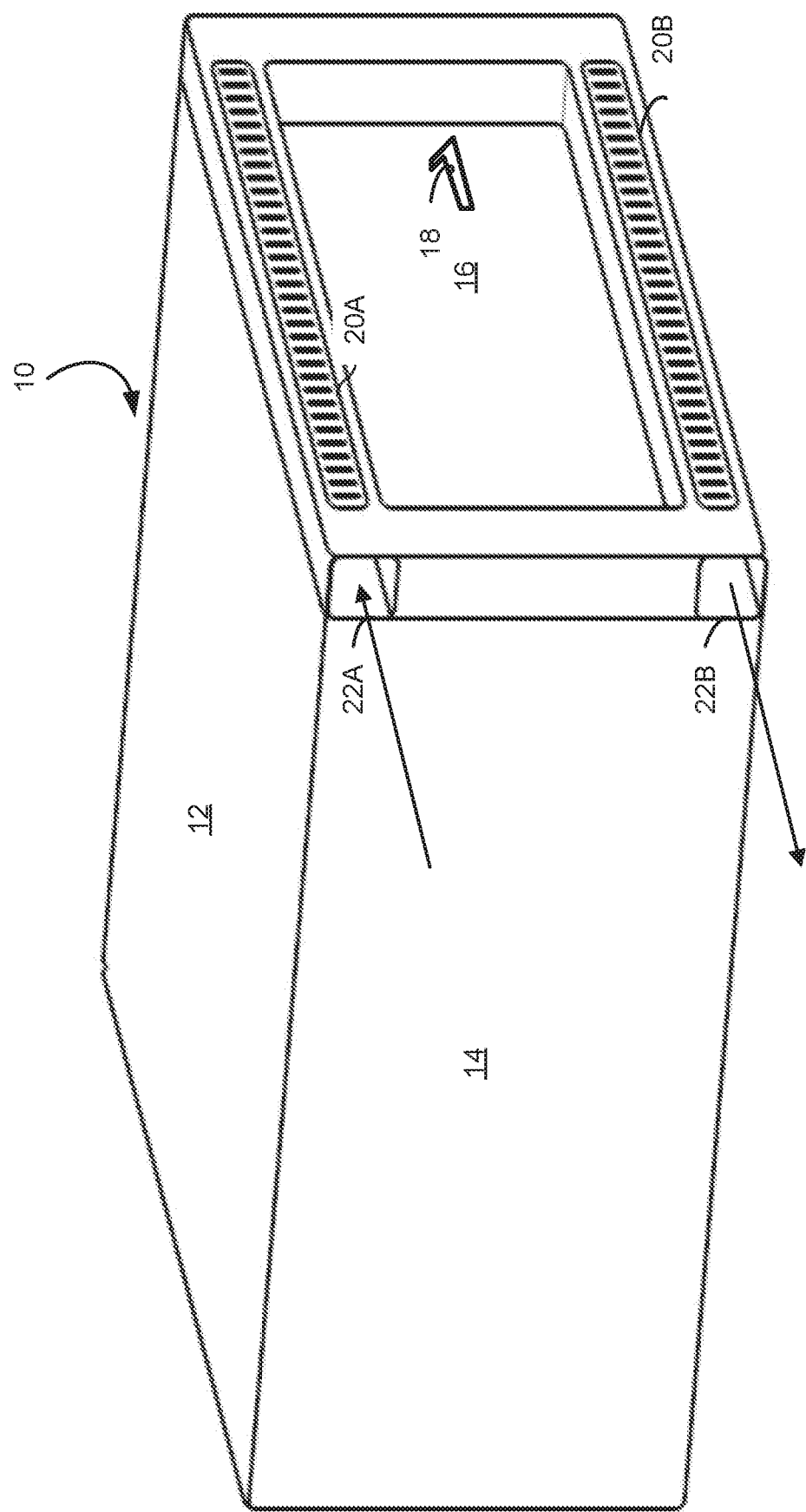
FIG. 1 is a perspective view of a capsule pod sleeping chamber in accordance with an embodiment of the present disclosure.

FIG. 1 depicts an exterior perspective view of a capsule pod sleeping chamber 10 of an embodiment in the present disclosure. As depicted in FIG. 1, the capsule pod sleeping chamber 10 may be an enclosure defined by a plurality of sides, including a top side 12, a left side 14, and a front side 16 pictured in FIG. 1. One of the sides may be configured to have a door or other openable and closable mechanism to allow ingress into and egress from the capsule pod sleeping chamber 10. While figures of the present disclosure illustrate capsule pod sleeping chambers with doors in front, it is contemplated that additionally or alternatively there may be a door on a different side of the capsule pod sleeping chambers. For example, in some embodiments, doors may be on the left and/or right sides of the capsule pod sleeping chamber 10 so as to make it easier for hospital attendants to access (e.g., lift in or out) a hospital patient inside the capsule pod sleeping chamber.

In various embodiments, the door is a hinged door that opens outwardly or inwardly, a roll-up door, or a sliding door. In some embodiments, the door or a different side of the capsule pod sleeping chamber 10 includes a window, which may or may not be openable (e.g., from the interior or exterior of the capsule pod sleeping chamber).

While the door is closed, the enclosure may be substantially hermetically sealed but for one or more interior vents (shown in FIG. 3), such as by negative pressure. In this manner, air within the capsule pod sleeping chamber 10 is substantially prevented from becoming contaminated by potential contaminants in a communal space outside the capsule pod sleeping chamber 10, and conversely air of the communal space may be substantially prevented from becoming contaminated by the air from the capsule pod sleeping chamber 10. In some implementations, the sides of the capsule pod sleeping chamber 10, including the door, are wholly or partially opaque. For example, one or more sides of the capsule pod sleeping chamber 10 may include a window whereby an occupant can see out or a facility staff member can see inside.

In some embodiments, the capsule pod sleeping chamber 10 has one or more side that outwardly face into a communal space. In some examples, a "communal space" or "communal area" refers to an area used or shared in common by an occupant of the capsule pod sleeping chamber 10 as well as other people in the vicinity, such as occupants of other capsule pod sleeping chambers and/or staff members employed by a facility hosting the capsule pod sleeping chamber 10. It is noted that the reference directions "left" and "right" are provided for ease of illustration only, and whether certain features of the capsule pod sleeping chamber 10 are on the left or right may be dependent upon the perspective of the viewer.

In some embodiments, the capsule pod sleeping chamber 10 has one or more vents 20A-20B in an exterior a side of the capsule pod sleeping chamber 10 that faces a communal space (e.g., the front). In some embodiments, at least one vent 20A of the one or more vents 20A-20B open into one or more ducts that are configured to draw in air from the communal space and exhaust the air away from the communal space or through a filter that filters out contaminants, such as dust, bacteria, and viruses prior to allowing the air back into the communal space. In some embodiments, at least another vent 20B of the one or more vents 20A-20B opens into one or more other ducts that are configured to supply, into the communal space, air from a source away from the communal space or air that has been filtered from contaminants, such as dust, bacteria, and viruses. Although the present disclosure makes reference to the exterior vents 20A-20B of the capsule pod sleeping chamber 10, it is contemplated that some embodiments of the capsule pod sleeping chambers 10 may lack the exterior vents 20A-20B and corresponding ducts and only have interior vents and ducts in the manner described in the present disclosure.

In some examples, a "duct" refers to a conduit or passage to deliver and/or remove air, such as supply air, return air, ventilation air, or exhaust air. A system of ducts may also be referred to as "ductwork." In some examples, a "vent" refers to an aperture, such as in a wall, that serves as an outlet or inlet to allow air to enter or leave a duct. In some embodiments, a vent has a number of slits or fins to prevent larger objects from going into the duct. In some of these embodiments, the slits or fins are adjustable so as to increase or decrease an amount of air flowing through the vent.

For example, the lower vent 20B located on the exterior of the lower end of a front face of the capsule pod sleeping chamber 10 in FIG. 1 may be configured to draw in air from the communal space and exhaust through the lower duct to another location. In the example, the upper vent 20A located on the exterior of the upper end of a front face of the capsule pod sleeping chamber 10 may be configured to supply clean air from another location into the communal space. Note that, in FIG. 1, the upper and lower ducts are illustrated as open to show that the ducts on the capsule pod sleeping chamber 10 can be connected to ducts that exhaust the air away from the communal space. In this manner, the capsule pod sleeping chamber 10 provides a benefit by mitigating the risk of contaminants (e.g., from coughs from ill persons in the communal space) entering the capsule pod sleeping chamber 10 by filtering out most contaminants before they have a chance to enter the capsule pod sleeping chamber 10. It is contemplated that the functions of the upper duct and lower duct can be reversed or be the same; for example, in some implementations, the lower vent 20B may be configured to supply air and the upper vent 20A may be configured to exhaust the air, or both vents 20A-20B may be configured to either supply air or exhaust air.

The capsule pod sleeping chamber 10 may be dimensioned such that it is wide enough and long enough to fit at least a standard twin bed mattress or a hospital twin bed mattress inside so a normal sized human being has enough room to lay down. The capsule pod sleeping chamber 10 may likewise be of a height that allows for a normal sized human being to sit upright on said mattress without their head touching the ceiling of the capsule pod sleeping chamber 10. For example, the capsule pod sleeping chamber 10 may be four feet wide, four feet high, and seven and a half feet long. It is contemplated that a capsule pod sleeping chamber may be larger or smaller as needed for a particular implementation. For example, the capsule pod sleeping chamber 10 may be larger so as, in addition to a bed, to accommodate a bookshelf and/or a small television. Or, as another example, the capsule pod sleeping chamber 10 may be dimensioned such that it is wide enough and long enough to fit at least a full, queen, or king sized mattress such that two people may comfortably occupy the capsule pod sleeping chamber 10 at the same time.

The capsule pod sleeping chamber 10 may be constructed of any of several types of materials. For example, at least some of the capsule pod sleeping chamber 10 may be comprised of acrylonitrile butadiene styrene (ABS) plastic. Additionally or alternatively, at least some of the capsule pod sleeping chamber 10 may be comprised of antimicrobial plastic or acrylic. Additionally or alternatively, at least some of the capsule pod sleeping chamber 10 may be comprised of fiberglass. In some embodiments, the capsule pod sleeping chamber 10 may be made of stamped steel for strength and to allow for stacking. In embodiments, the capsule pod sleeping chamber 10 is coated in a protective finish such as paint or plating to prevent corrosion. In some embodiments, the capsule pod sleeping chamber 10 includes 1 wires and/or other components for an electric light, an electrical outlet, Ethernet connection, fiber optic connection, audio speaker, an alarm (e.g., smoke, fire, etc.), call button, medical monitoring device, or other such functionality. In some embodiments, the capsule pod sleeping chamber may have connections for connecting an oxygen tank and/or oxygen mask to provide oxygen to a patient inside the capsule pod sleeping chamber. Similarly, in some embodiments the capsule pod sleeping chamber may be configured with connections to accommodate intravenous (IV) therapy for a patient within the capsule pod sleeping chamber.

Figure 2:
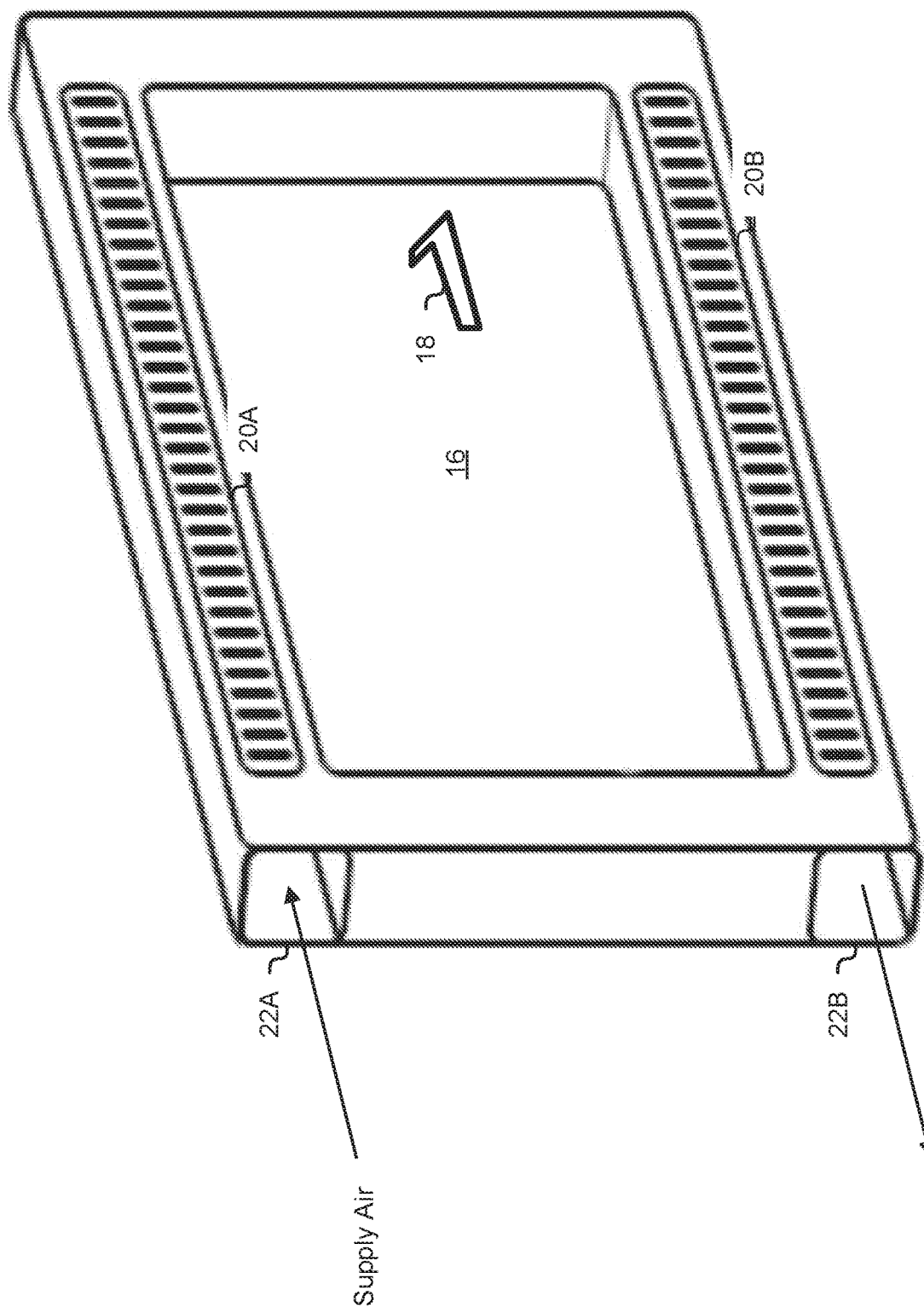
FIG. 2 is a perspective view of exterior venting of a capsule pod sleeping chamber in accordance with an embodiment of the present disclosure.

FIG. 2 depicts an exterior perspective view of a side of a capsule pod sleeping chamber that has exterior vents 20A-20B for supplying and exhausting air in the immediate vicinity of the capsule pod sleeping chamber, such as the capsule pod sleeping chamber of FIG. 1. The side of the capsule pod sleeping chamber depicted in FIG. 2 is illustrated to be a front side 16, but it is contemplated that the side may be another side, such as the left side 14 or the right side 28. In some embodiments, a door or other entrance into and out of the capsule pod sleeping chamber may be located on a same side as the exterior vents 20A-20B, as depicted in FIG. 2. The door, when closed, may substantially hermetically seal (e.g., by negative pressure between the interior of the capsule pod sleeping chamber 10 and the air outside of the capsule pod sleeping chamber 10) the capsule pod sleeping chamber from air in a common space outside the capsule pod sleeping chamber. The door may have a handle 18 or other mechanism for opening the door for ingress into or egress out of the capsule pod sleeping chamber.

In embodiments, the exterior vents 20A-20B may be apertures that open into ducts 22A-22B for exhaust air and/or supply air. The embodiment depicted in FIG. 2 illustrates an upper vent 20A that provides supply air from a supply air duct 22A and a lower vent 20B that draws away exhaust air through an exhaust air duct 22B. However, other implementations are contemplated such as where both upper and lower vents 20A-20B supply air or where both upper and lower vents 20A-20B exhaust air. Additionally or alternatively, the exterior vents 20A-20B and interior ducts 22A-22B may be vertical or in some other orientation other than the horizontal orientation depicted in FIG. 2. Although the present disclosure makes reference to interior vents of the capsule pod sleeping chamber 10, it is contemplated that the exterior vents 20A-20B and corresponding ducts 22A-22B described in the present disclosure provide separate advantages and benefits and may be implemented with capsule pod sleeping chambers that lack interior vents and ducts in the manner described in the present disclosure.

In some embodiments, the capsule pod sleeping chamber 10 includes a fan or other blower for moving the air through one or more of the ducts 22A-22B. In some embodiments, the capsule pod sleeping chamber ducts or the vents 20A-20B include one or more filters for filtering contaminants from the communal space.

Figure 3:
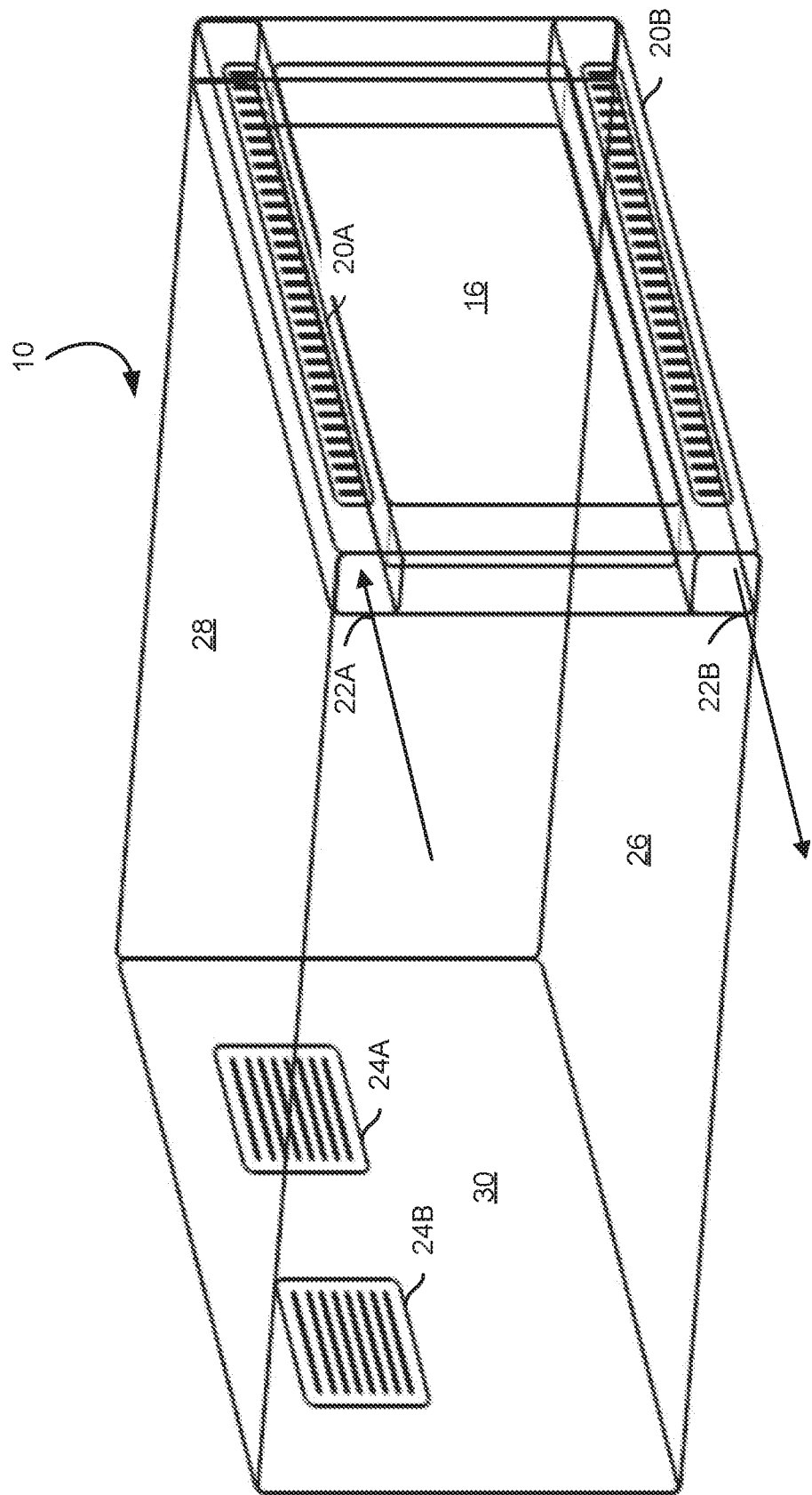
FIG. 3 is perspective view of an interior of a capsule pod sleeping chamber in accordance with an embodiment of the present disclosure.

FIG. 3 depicts an interior perspective view of the capsule pod sleeping chamber 10 of an embodiment in the present disclosure. As depicted in FIG. 3, the interior of the capsule pod sleeping chamber 10 includes a plurality of sides, including a floor 26, a right side 28, the front side 16, and rear side 30. In embodiments, the capsule pod sleeping chamber 10 has a plurality of vents 20A-20B and 24A-24B. The embodiment illustrated in FIG. 3 depicts two interior vents 24A-24B, both of which are located on the rear side 30 of the capsule pod sleeping chamber 10. However, it is contemplated that other arrangements are possible, such as an interior vent on the right side 28 and another interior vent on the left side 13, and so on. Of the plurality of vents 20A-20B and 24A-24B, at least one may be a supply air vent and at least another may be an exhaust air vent. The interior vents 24A-24B may open into connected to ducts, such as in the manner illustrated in FIG. 5.

In some embodiments, the capsule pod sleeping chamber 10 has one or more environmental controls whereby an occupant of the capsule pod sleeping chamber 10 can control the rate of airflow inside the capsule pod sleeping chamber 10 and/or heat or cooling provided by interior vents. In embodiments, the capsule pod sleeping chamber 10 may have exterior vents 20A-20B such as shown in FIG. 3. The exterior vents 20A-20B may be connected to different ducts 22A-22B from the ducts to which the interior vents 24A-24B open into.

In some embodiments, the capsule pod sleeping chamber 10 may include an adjustable bed mechanism, such as a hinged mechanism that can cause a mattress on top of the mechanism to form into different positions. For example, the adjustable bed mechanism may incline the head portion of a mattress and/or raise the foot portion of the mattress independently of the head portion. The adjustable bed mechanism may or may not be motorized. In some embodiments, the capsule pod sleeping chamber is configured to accommodate a gurney so that a patient may be easily rolled into or out of the capsule pod sleeping chamber through a front or side entrance.

Figure 4:
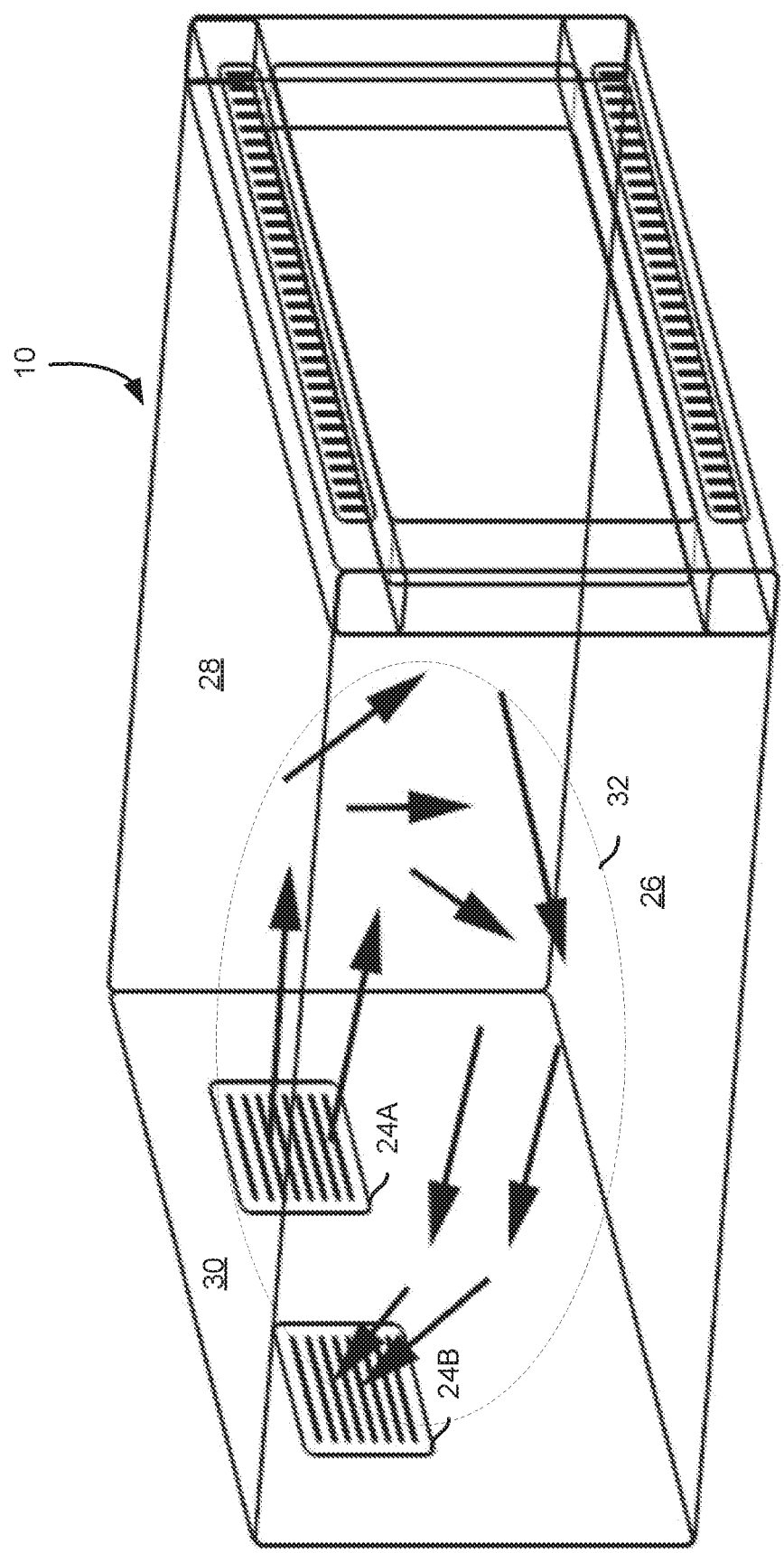
FIG. 4 is a perspective view of airflow and interior venting of an interior of a capsule pod sleeping chamber in accordance with an embodiment of the present disclosure.

FIG. 4 depicts a perspective interior view of the capsule pod sleeping chamber 10 of an embodiment of the present disclosure, similar to the view of the capsule pod sleeping chamber 10 of FIG. 3 but illustrating airflow through the interior vents 24A-24B. As can be seen in FIG. 4, a supply air vent is in fluid communication with an interior of the capsule pod sleeping chamber 10 so as to permit air 32 to be supplied from a supply air duct into the capsule pod sleeping chamber 10. Likewise, an exhaust air vent is in fluid communication with the interior of the capsule pod sleeping chamber 10 so as to permit the air 32 to be exhausted from the capsule pod sleeping chamber 10 into an exhaust air duct.

In some embodiments, the capsule pod sleeping chamber 10 includes one or more sensors for measuring air quality within the capsule pod sleeping chamber 10. In such embodiments, the one or more sensors may be communicatively coupled to a device that regulates the air flow in accordance with the one or more sensors' measure of the air quality. For example, if the device that regulates the airflow determines that the one or more sensors have detected that air within the capsule pod sleeping chamber 10 contains an amount greater than a certain threshold of particulates per volume, the device cause (e.g., by speeding up a fan in a duct) the air flowing in and out through the vents 24A-24B to increase so as to better clear the contaminated air from the capsule pod sleeping chamber 10. Conversely, if device that regulates the airflow determines that the one or more sensors have detected that the particulate amount is below a certain threshold, the device may cause (e.g., by slowing down a fan in a duct) the air flowing in and out to decrease, so as to conserve energy, reduce noise, and so on.

Figure 5:
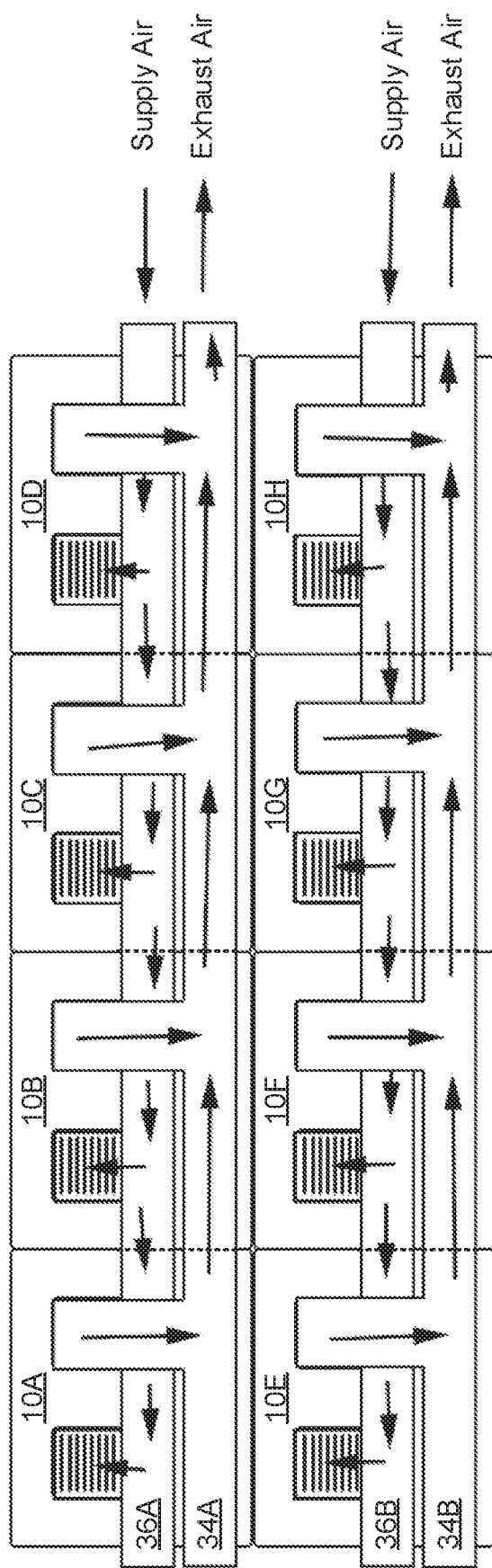
FIG. 5 is a rear view of airflow and venting of a series of stacked capsule pod sleeping chambers in accordance with an embodiment of the present disclosure.

FIG. 5 depicts ductwork attached to interior vents 24A-24B of capsule pod sleeping chambers of an embodiment of the present disclosure. Specifically, FIG. 5 illustrates ductwork for a set of eight capsule pod sleeping chambers 10A-10I (e.g., a top row of four capsule pod sleeping chambers 10A-10D stacked on top of a bottom row of four capsule pod sleeping chambers 10E-10H), each with a pair of vents 24A-24B such as shown in FIGS. 3 and 4. The capsule pod sleeping chambers 10A-10H may be constructed so that their exhause air ducts 34A-34B and supply air ducts 36A-36B can mate with respective exhaust air and supply air ducts 34A-34B and 36A-36B of adjacent capsule pod sleeping chambers. For example, each of the ends of the ducts for each capsule pod sleeping chamber 10 may have a flange that could be capped (e.g., to terminate the duct) or could be butted up to another duct (e.g., with a gasket between) of an adjacent capsule pod sleeping chamber. In this manner, the connected ducts may form a continuous duct for the connected capsule pod sleeping chambers. As illustrated in FIG. 5, one end of the ducts 34A-34B and 36A-36B may go to the source of supply air or destination of exhaust air, while the other end of the ducts 34A-34B and 36A-36B may be capped to prevent air from escaping out the other side. Note that while the ducts are illustrated in FIG. 5 to be external to the capsule pod sleeping chambers 10A-10H, it is contemplated that the ducts are built-into the walls of the capsule pod sleeping chambers 10A-10H in some embodiments.

In a variation, for example, the exhaust air duct 34B at one end may be connected to the exhaust air duct 34B at the same end, and the other end of either the exhaust air duct 34A or the exhaust air duct 34A may be capped. Likewise, one end of the supply air duct 36B at one end may be connected to the supply air duct 36A at the same end, and the other end of either the supply air duct 36A or the supply air duct 36B may be capped. In this manner, the exhaust air ducts 34A-34B and/or the supply air ducts 36A-36B may be formed into continuous ducts for both the top row and bottom row of capsule pod sleeping chambers 10A-10H.

The dotted lines in FIG. 5 illustrate the points at which the ducts may be connected together. In some embodiments, one or more other connections (e.g., electrical conduit, Ethernet, antenna, etc.) within each capsule pod sleeping chamber can also be mated to share such connections with an adjacent capsule pod sleeping chamber. In this manner, each capsule pod sleeping chamber is modular and may stand alone or may interface with other capsule pod sleeping chambers in various configurations.

As can be seen in FIG. 5, air in the supply air ducts 34A-34B and air in the exhaust air ducts are isolated from each other. Further, the exhaust air ducts may exhaust the air at a location that is separated from the common space immediately outside the capsule pod sleeping chambers 10A-10H so as to reduce the risk of contaminating air in the common space with the exhaust air of the capsule pod sleeping chambers 10A-10H. Likewise, the supply air ducts 36A-36B may supply the air from a location that is separated from the common space immediately outside the capsule pod sleeping chambers 10A-10H so as to reduce the risk of contaminating the air of the capsule pod sleeping chambers 10A-10H with potentially contaminated air from the common space.

In some embodiments, filters are additionally or alternatively located within the ducts 34A-34B and/or 36A-36B (e.g., at the supply air vents, at the destination end of the exhaust air ducts 34A-34B, at the supply end of the supply air ducts 36A-36B, etc.). In some embodiments, such filters may be high-efficiency particulate air (HEPA) filters satisfying the American Society of Mechanical Engineers (ASME) HEPA standard of removing 99.97% of airborne 0.3 micrometers (μm) in diameter or European HEPA standard of removing 99.95% of airborne 0.3 μm in diameter. In some embodiments, the capsule pod sleeping chamber configuration additionally or alternatively employ ultraviolet (UV) light, such as UVC, to irradiate and disinfect the air passing through the ducting. In some embodiments, the capsule pod sleeping chamber 10 includes a fan or other blower for moving the air through one or more of the ducts 34A-34B or 36A-36B.

In embodiments, the vents are adjustable so as to manage the proper air flow for each of the capsule pod sleeping chambers 10A-10H. Using FIG. 5 as an example, in implementations where each duct only has a single fan routing air through the duct, with all of the vents fully open, capsule pod sleeping chambers 10D and 10H may experience the greatest exchange of air due to being closer to fans, whereas the capsule pod sleeping chambers 10A and 10E may experience the weakest exchange of air. Thus, the adjustable vents may be narrowed to reduce the airflow of capsule pod sleeping chambers closer to fans and widened to increase airflow of capsule pod sleeping chambers farther from the fans so as to equalize the air exchange among all capsule pod sleeping chambers of the set. In some embodiments, the adjustments to the vents may be made with a movable or removable slotted backing plate behind the grill of the vent. In some embodiments, the vent adjustment additionally or alternatively may be made by a mechanism that changes the angle of the fins of the vent grill so that an occupant of the capsule pod sleeping chamber can change the airflow within their capsule pod sleeping chamber according to a personal level of comfort.

Figure 6:
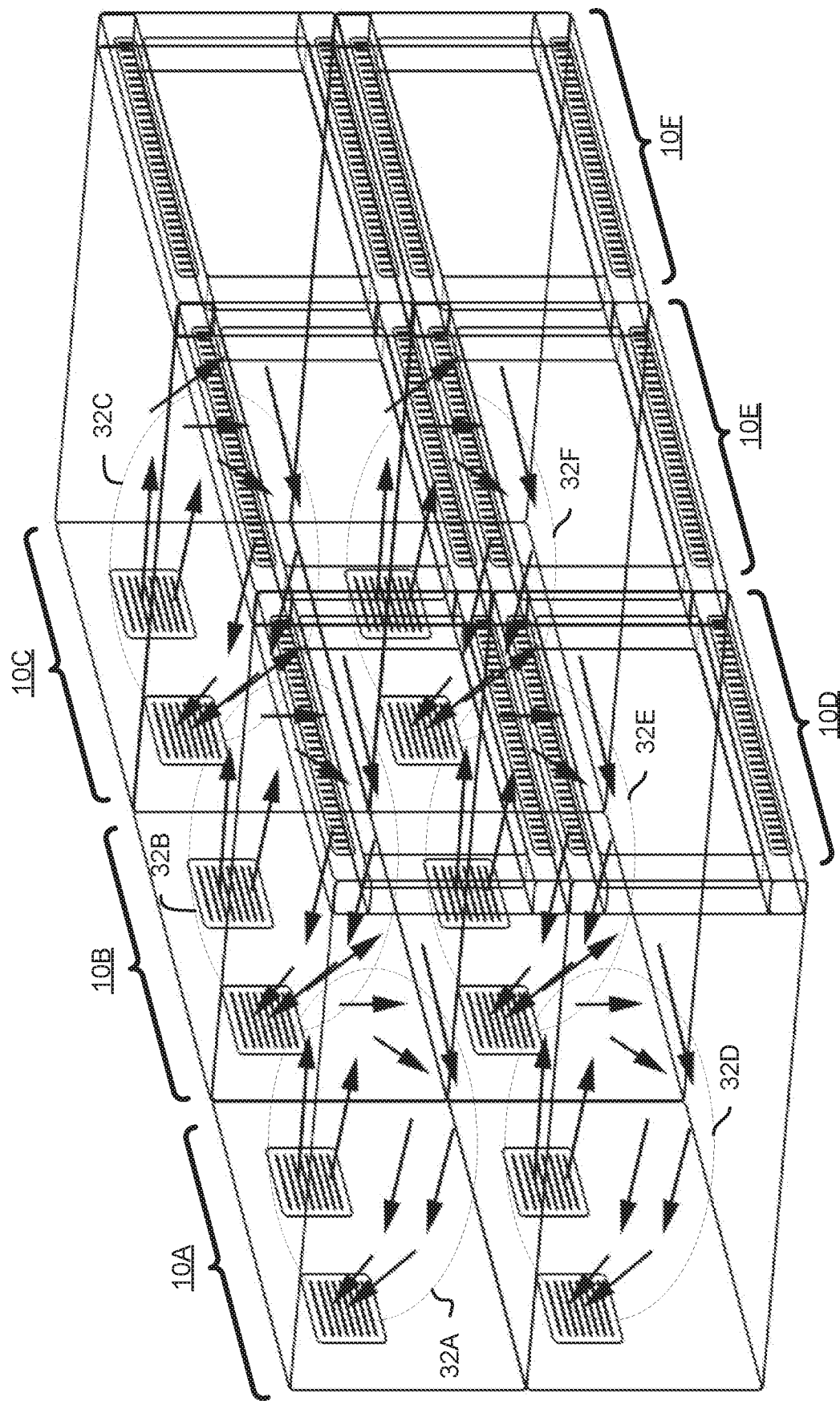
FIG. 6 is a perspective view of airflow and interior venting of a series of stacked capsule pod sleeping chambers in accordance with an embodiment of the present disclosure.

FIG. 6 depicts a perspective interior view of a set of stacked capsule pod sleeping chambers 10A-10F of an embodiment of the present disclosure. Specifically, FIG. 6 depicts a row of three upper capsule pod sleeping chambers 10A-10C stacked on top of a row of three lower capsule pod sleeping chambers 10D-10F. As can be seen in FIG. 6, the interior of each of the capsule pod sleeping chambers 10A-10F is in fluid communication with a respective supply air vent and exhaust air vent to circulate the air 32A-32F in. In this manner, contaminant-free supply air is provided individually to each of the capsule pod sleeping chambers 10A-10F, and exhaust air is likewise individually exhausted from each of the capsule pod sleeping chambers 10A-10F.

Figure 7:
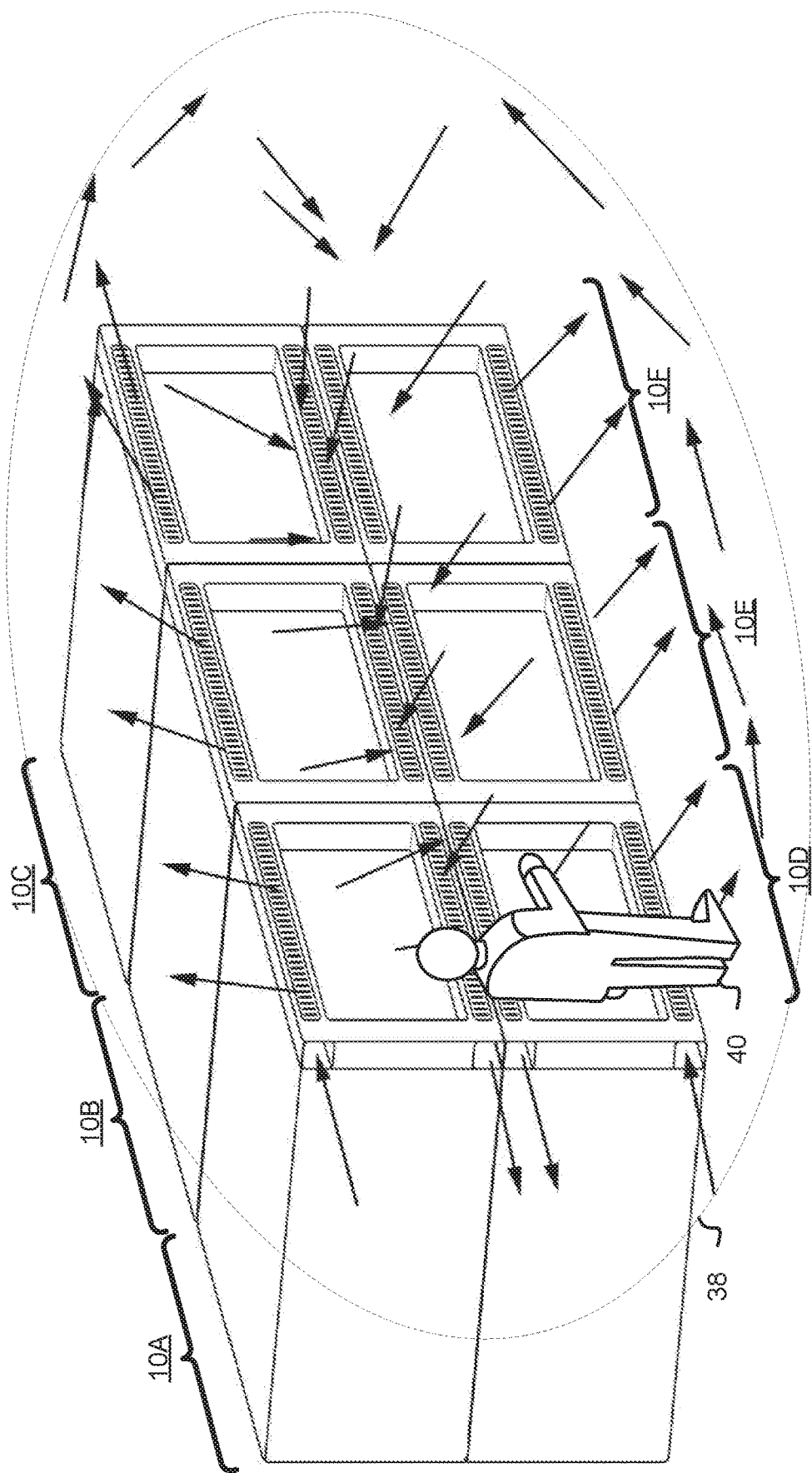
FIG. 7 is a perspective view of airflow and exterior venting of a series of stacked capsule pod sleeping chambers in accordance with an embodiment of the present disclosure.

FIG. 7 depicts an exterior perspective view of a set of stacked capsule pod sleeping chambers of an embodiment of the present disclosure. Specifically, FIG. 7 depicts a row of three upper capsule pod sleeping chambers 10A-10C stacked on top of a row of three lower capsule pod sleeping chambers 10D-10F, such as those depicted in FIG. 6. The each of the set of stacked capsule pod sleeping chambers may have exterior vents, as depicted in FIG. 2, for supplying and exhausting air 38 of a common space in the immediate vicinity of the capsule pod sleeping chamber. Although other configurations are contemplated, note that the bottom vents of the upper row of capsule pod sleeping chambers 10A-10C and the top vents of the bottom row are exhaust vents in the implementation depicted in FIG. 7. Conversely, the upper vents of the upper row of capsule pod sleeping chambers 10A-10C and the bottom vents of the bottom row of capsule pod sleeping chambers 10D-10F are supply vents in this implementation. By placing the exhaust vents near to the level of an average-sized person's head, bacteria, viruses, or other contaminants that become aerosolized from coughs, sneezes, exhalations, or other emissions by a person 40 in the common space will get directly drawn into the exhaust vents in this implementation. In this manner, if an aerosol is created, it may be removed at a base of a capsule pod sleeping chamber near where was created, so that even if a door of one of the capsule pod sleeping chambers 10A-10F is opened, much of the air 38 entering through the doorway into the capsule pod sleeping chamber should still be substantially contaminant-free. Similarly, much of the air escaping from the capsule pod sleeping chamber into the common space through an open door should be drawn into the exterior exhaust vent, thereby reducing the possibility of introducing contaminated air from the capsule pod sleeping chamber into the common space. Clean, contaminant-free air then may be supplied into the common space via the supply vents.

As with the ducts for the interior vents, the capsule pod sleeping chambers 10A-10F may be constructed so that their supply air ducts and exhaust air ducts can mate with respective supply air and exhaust air ducts and of adjacent capsule pod sleeping chambers. For example, each of the ends of the ducts for each of the capsule pod sleeping chambers 10A-10F may have a flange that could be capped (e.g., to terminate the duct) or could be butted up to another duct (e.g., with a gasket between) of an adjacent capsule pod sleeping chamber. In this manner, the connected ducts may form a continuous duct for the connected capsule pod sleeping chambers.

In embodiments, the exterior vents are adjustable so as to manage the air flow. For example, with all of the vents fully open, the vents at one end of a row of capsule pod sleeping chambers may experience the greatest exchange of air due to being closer to fans, whereas the vents at the opposite end of the row of capsule pod sleeping chambers may experience the weakest exchange of air. Thus, the adjustable vents may be adjusted to equalize airflow of all exterior vents of the capsule pod sleeping chambers. In some embodiments, the adjustments to the vents may be made with a movable or removable slotted backing plate behind the grill of the vent. Note that the features described for the interior vents and ductwork for the interior vents may be applicable to the exterior vents and ductwork for the exterior vents, and vice versa.

Figure 8:
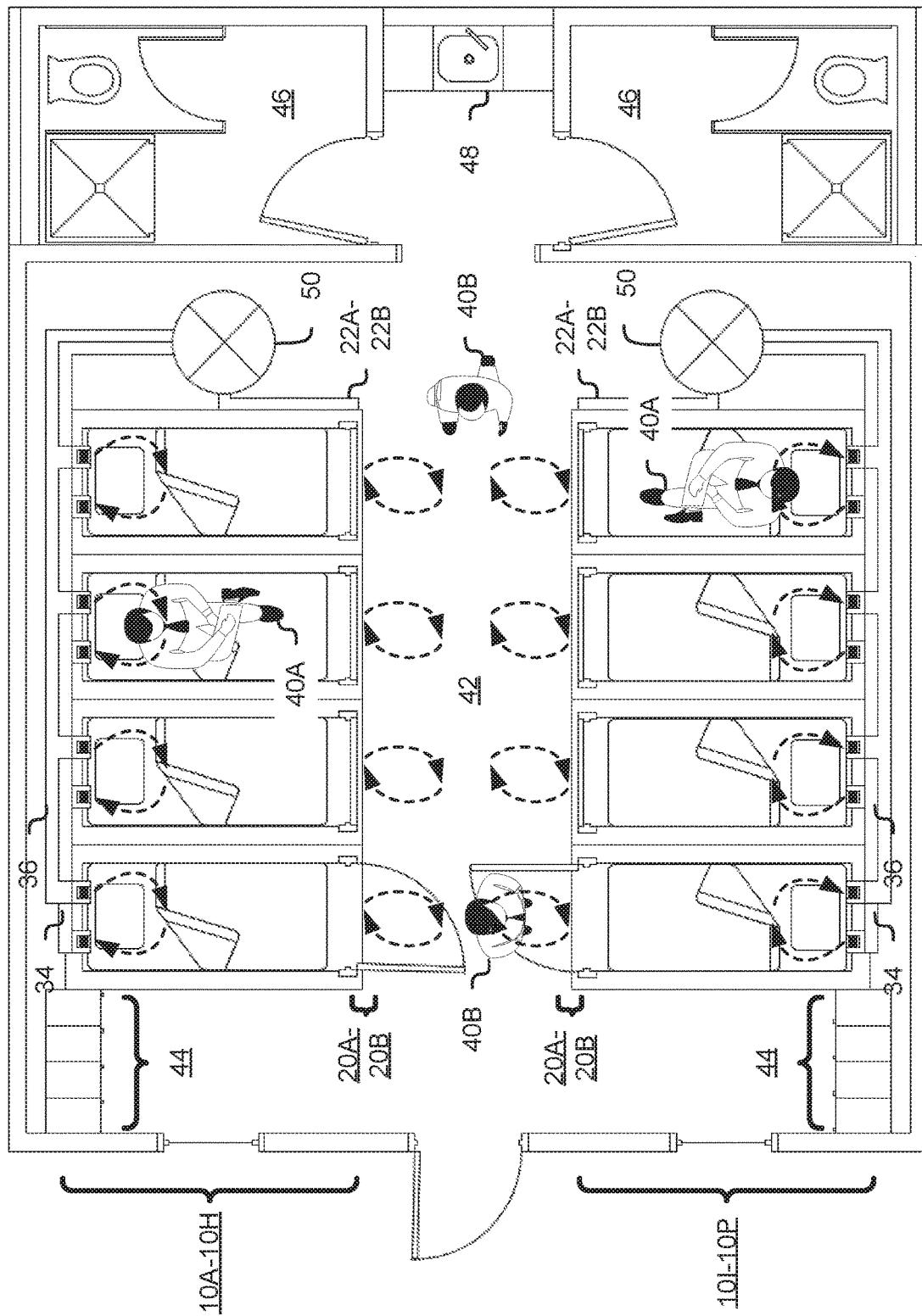
FIG. 8 is an overhead view of an installation of a set of capsule pod sleeping chambers in a room in accordance with an embodiment of the present disclosure.

FIG. 8 depicts an overhead cross-sectional view of an implementation of capsule pod sleeping chambers of the present disclosure. As depicted in FIG. 8, a set of capsule pod sleeping chambers 10A-10P comprising a first subset of capsule pod sleeping chambers 10A-10H and a second subset of capsule pod sleeping chambers 10I-10P has been installed in a room having common spaces 42 allowing movement of individuals in the room. Each of the set of capsule pod sleeping chambers 10A-10P are shown to be connected to supply air ducts 36 and exhause air ducts 34 that exhaust and supply air via vents located within the capsule pod sleeping chambers 10A-10H and on exteriors of the capsule pod sleeping chambers 10A-10H as described in the present disclosure. It is contemplated that the set of capsule pod sleeping chambers 10A-10P may be vertically stacked, such as those shown in FIGS. 5-7. Thus, although only eight capsule pod sleeping chambers are visible in FIG. 8 from the overhead cross-sectional view, it is contemplated that there may be at least another eight capsule pod sleeping chambers directly below the ones seen, for a total of at least sixteen capsule pod sleeping chambers in the set in a room such as the one depicted in FIG. 8.

The room, as depicted, includes common areas for lockers 44 and common bathrooms 46 and sink 48. Note that the configuration depicted in FIG. 8 is for illustrative purposes only, and various other implementations are contemplated as being within the scope of the present disclosure. In this implementation the exhaust and supply air ducts 34 and 36 are coupled to a pair of air purifier units 50 that remove contaminants (e.g., viruses, bacteria, dust, and/or other contaminants) from the exhaust air and provide filtered air to the supply air ducts 34 without intermixing either with air from the common space 42. In another implementation, the exhaust and supply air ducts 34 and 36 could route air to and/or from a location outside the room.

In some embodiments, an "air purifier unit" may refer to a device that removes contaminants from air to improve indoor air quality. An air purifier unit may employ one or more purifying techniques such as forcing air through a HEPA filter, filtering air through a high-efficiency Minimum Efficiency Reporting Value (MERV) 14 filter or higher, ultraviolet germicidal irradiation (UVGI), activated carbon, a polarized electric field, photocatalytic oxidation, charged air or gas ions, immobilized cell technology, ozone generation, titanium dioxide technology, or thermodynamic sterilization.

In this manner, individuals 40A with doors of their capsule pod sleeping chambers 10C and 10H closed, thereby substantially hermetically sealing their capsule pod sleeping chambers 10C and 10H but for the interior air vents, are protected from potentially contaminated air in the common space 42 (e.g., potentially contaminated by coughing or sneezing of one or both individuals 40B). Further, the exterior vents 20A-20B recycle the potentially contaminated air from the common space 42, thereby diminishing the risk of contaminated air entering a capsule pod sleeping chamber when the door is opened (such as capsule pod sleeping chambers 10A and 10D) and diminishing the risk of potentially contaminated air from such capsule pod sleeping chambers mixing with the air of the common space 42. Thus, multiple capsule pod sleeping chambers can be used to provide healthy and private accommodations in a small space for several individuals in a manner similar to that depicted in FIG. 8.

Figure 9:
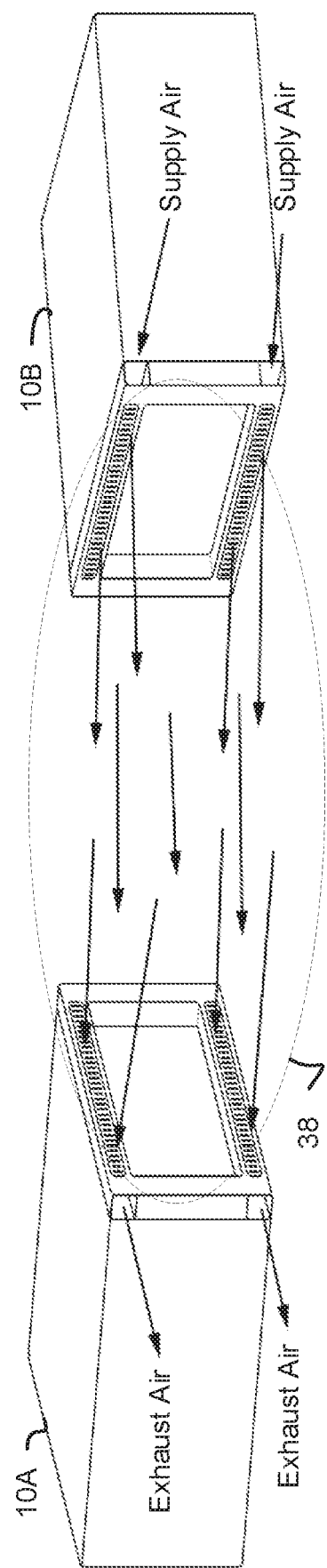
FIG. 9 is a perspective view of airflow and exterior venting of a pair of facing capsule pod sleeping chambers in accordance with an embodiment of the present disclosure.

FIG. 9 depicts a perspective view of a pair of capsule pod sleeping chambers in an alternate configuration. Specifically, FIG. 9 depicts a first capsule pod sleeping chamber 10A that faces a second capsule pod sleeping chamber 10B. In the configuration depicted in FIG. 9, vents and ducts of the first capsule pod sleeping chamber 10A have been configured to exhaust air, while vents and ducts of the second capsule pod sleeping chamber 10B have been configured to supply air. In this manner, the air 38 in the common air space flows in the direction from the second capsule pod sleeping chamber 10B toward the first capsule pod sleeping chamber 10A. Thus, if this configuration were implemented in the room of FIG. 8, the air 38 could be supplied by the exterior vents 20A-20B of the first subset of capsule pod sleeping chambers 10A-10H and the air 38 could travel toward the exterior vents 20A-20B of the second subset of capsule pod sleeping chambers 10I-10P, where it could be exhausted to the air purifier unit.

Figure 10:
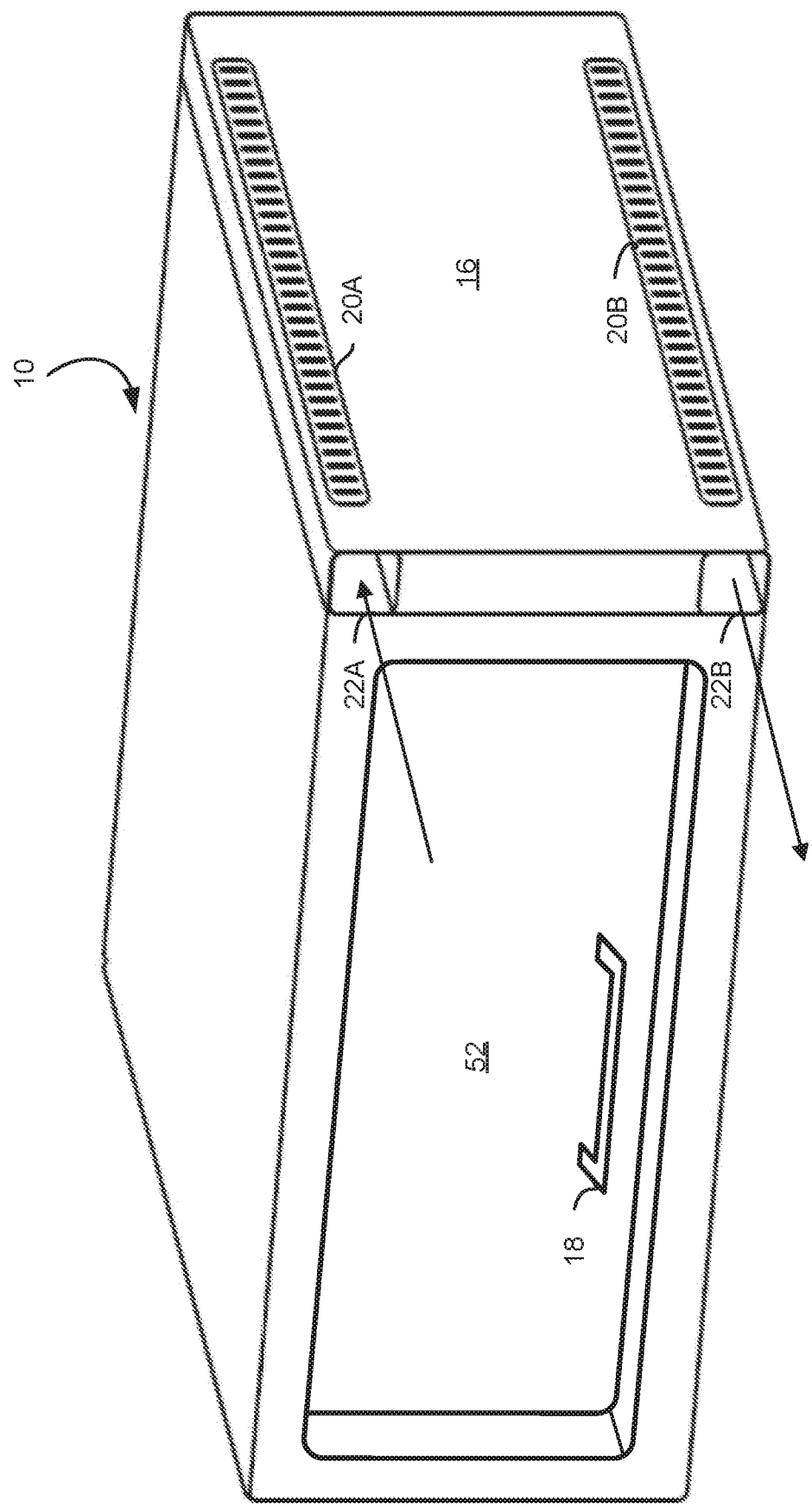
FIG. 10 is a perspective view of a capsule pod sleeping chamber in accordance with an alternate embodiment of the present disclosure.

FIG. 10 depicts an exterior perspective view of a capsule pod sleeping chamber 10 of an alternate embodiment in the present disclosure. The capsule pod sleeping chamber 10 depicted in FIG. 10 exterior vents 20A-20B and ducts 22A-22B similar to the capsule pod sleeping chamber of FIG. 1, but has a side door 52 along a long side of the capsule pod sleeping chamber, rather than at the front side 16 (although it is contemplated that the door of the capsule pod sleeping chamber 10 in FIG. 10 may be in addition to a door on the front side). The long side may be adjacent to a wall that includes one or more interior vents. The side door 52 may have a handle 18 for opening the door, and may be configured with a mechanism to allow ingress into and egress from the capsule pod sleeping chamber 10. In various embodiments, the side door 52 is a hinged door that opens outwardly or inwardly, a roll-up door, or a sliding door. In some embodiments, the side door 52 includes a window, which may or may not be openable (e.g., from the interior or exterior of the capsule pod sleeping chamber 10). While the side door 52 is closed, the enclosure may be substantially hermetically sealed but for one or more interior vents. In some implementations, the side door is wholly or partially opaque.

The embodiment illustrated in FIG. 10 illustrates one of many possible arrangements of a door and exterior vent. However, it is contemplated that other arrangements are possible, such as an exterior vents on the right or left side in addition or alternative to the vents on the front side 16. It is contemplated that the vents may run vertically instead of horizontally or that more than two vents may appear on the exterior of the capsule pod sleeping chamber 10. For example, in an alternative implementation, exhaust air and supply air vents may be present above and below the side door 52, and an additional pair of exhaust air and side air vents may be running vertically on the front face (the ducts of which may be connected to an adjacent capsule pod sleeping chamber above or below the capsule pod sleeping chamber 10).

FIG. 11 is a flowchart illustrating an example of a process 1100 for filtration of air in a capsule pod sleeping chamber in accordance with various embodiments. The process 1100 may be applicable to the utilization of the capsule pod sleeping chamber as depicted in FIG. 1 and throughout the present disclosure. The process 1100 may include a series of operations wherein the capsule pod sleeping chamber is substantially hermetically sealed from a common space, filtered air is supplied into the capsule pod sleeping chamber in isolation from common space air, and exhaust air is exhausted in isolation from the common space air.

In 1102, the interior of the capsule pod sleeping chamber is substantially sealed away from the air of a common space outside the capsule pod sleeping chamber, such as by closing the door of the capsule pod sleeping chamber. The door of the capsule pod sleeping chamber may make a seal with the doorway of the capsule pod sleeping chamber such that air from the common space is effectively prevented from infiltrating the capsule pod sleeping chamber.

In 1104, a supply air vent in fluid communication with an interior of the capsule pod sleeping chamber supplies filtered, sterilized, or otherwise microbe-free air into the capsule pod sleeping chamber via a supply air duct. As has been described in the present disclosure, the supply air duct provides the supply air in isolation from the air of the common space so as not to potentially contaminate the air being supplied to the capsule pod sleeping chamber. In some embodiments, the supply air may be filtered air from an air purifier unit. In other embodiments, the supply air may originate from an area outside the common space in which the capsule pod sleeping chamber is located.

In 1106, exhaust air of the capsule pod sleeping chamber is exhausted through an exhaust air vent in fluid communication with an interior of the capsule pod sleeping chamber in isolation from the common space so as not to potentially contaminate common space air with contaminants from the capsule pod sleeping chamber. In some embodiments, the exhaust air may be routed to an air purification unit to filter, sterilize, or otherwise purify the exhaust air, rendering it suitable to be resupplied to the capsule pod sleeping chamber as supply air. In other embodiments, the exhaust air may be routed to some area outside the common space in which the capsule pod sleeping chamber is located.

FIG. 12 is a flowchart illustrating an example of a process 1200 for utilizing exterior vents of a capsule pod sleeping chamber for filtration of air in a common space in accordance with various embodiments. The process 1200 may be applicable to the utilization of the capsule pod sleeping chamber depicted in FIG. 7 and throughout the present disclosure. The process may include a series of operations wherein air is exhausted from and supplied to a common space via ducts on a side of the capsule pod sleeping chamber.

In 1202, air from the common space is drawn into an exhaust air duct via an exhaust air vent on an exterior side of a capsule pod sleeping chamber. The air drawn into the exhaust air duct may be routed to an area separated from the common space and from the capsule pod sleeping chamber, such as to an air purifier unit or to an area outside the common space. In embodiments, the air routed to the area separated from the common space may be filtered, sterilized, or otherwise rendered free from one or more contaminants, such as viruses, bacteria, dust, or the like.

In 1204, exhaust air is disinfected, such as by UV lights, a HEPA filter, or an air purifier unit, thereby producing supply air that may be recirculated to the capsule pod sleeping chamber in 1206. In 1206, air is supplied to the common space from a supply air duct via a supply air vent on an exterior side of the capsule pod sleeping chamber. The air supplied by the supply air duct may be obtained from an area separated from the common space and from the capsule pod sleeping chamber, such as the same or other air purifier unit to which the exhaust air is routed or from some other area outside the common space. In embodiments, the supply air has been filtered, sterilized, or otherwise rendered free from one or more contaminants, such as viruses, bacteria, dust, or the like.

The supply air vent and the exhaust air vent may therefore be in fluid communication with the common space. It is noted that one or more of the operations performed in 1202-04 may be performed in different order than illustrated in FIG. 12.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms. For example, the use of the terms "a," "an," and "the" and similar referents in the context of describing the disclosed embodiments (especially in the context of the following claims) are to be construed to cover both the singular and the plural, unless otherwise indicated or clearly contradicted by context. Similarly, use of the term "or" is to be construed to mean "and/or" unless contradicted explicitly or by context. The terms "comprising," "having," "including," and "containing" are to be construed as open-ended terms (i.e., meaning "including, but not limited to,") unless otherwise noted.

The term "connected," where unmodified and referring to physical connections, is to be construed as partly or wholly contained within, attached to, or joined together, even if there is something intervening. Recitation of ranges of values are merely intended to serve as a shorthand method of referring individually to each separate value falling within the range, unless otherwise indicated and each separate value is incorporated into the specification as if it were individually recited. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal. The use of the phrase "based on," unless otherwise explicitly stated or clear from context, means "based at least in part on" and is not limited to "based solely on."

Conjunctive language, such as phrases of the form "at least one of A, B, and C," or "at least one of A, B and C," (i.e., the same phrase with or without the Oxford comma) unless specifically stated or otherwise clearly contradicted by context, is otherwise understood with the context as used in general to present that an item, term, etc., may be either A or B or C, any nonempty subset of the set of A and B and C, or any set not contradicted by context or otherwise excluded that contains at least one A, at least one B, or at least one C. For instance, in the illustrative example of a set that has three members, the conjunctive phrases "at least one of A, B, and C" and "at least one of A, B and C" refer to any of the following sets: {A}, {B}, {C}, {A, B}, {A, C}, {B, C}, {A, B, C}, and, if not contradicted explicitly or by context, any set that has {A}, {B}, and/or {C} as a subset (e.g., sets with multiple "A"). Thus, such conjunctive language is not generally intended to imply that certain embodiments require at least one of A, at least one of B and at least one of C each to be present. Similarly, phrases such as "at least one of A, B, or C" and "at least one of A, B or C" refer to the same as "at least one of A, B, and C" and "at least one of A, B and C" refer to any of the following sets: {A}, {B}, {C}, {A, B}, {A, C}, {B, C}, {A, B, C}, unless differing meaning is explicitly stated or clear from context. In addition, unless otherwise noted or contradicted by context, the term "plurality" indicates a state of being plural (e.g., "a plurality of items" indicates multiple items). The number of items in a plurality is at least two, but can be more when so indicated either explicitly or by context.

It should be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" or "one or more" to introduce claim recitations. However, the use of such phrases do not imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Accordingly, the invention is not limited except as by the appended claims.

The use of any examples, or exemplary language (e.g., "such as") provided, is intended merely to better illuminate embodiments of the invention and does not pose a limitation on the scope of the invention unless otherwise claimed. No language in the specification should be construed as indicating any non-claimed element as essential to the practice of the invention.

Embodiments of this disclosure are described, including the best mode known to the inventors for carrying out the invention. Variations of those embodiments may become apparent to those of ordinary skill in the art upon reading the foregoing description. The inventors expect skilled artisans to employ such variations as appropriate and the inventors intend for embodiments of the present disclosure to be practiced otherwise than as specifically described. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated or otherwise clearly contradicted by context.

All references, including publications, patent applications, and patents, cited are hereby incorporated by reference to the same extent as if each reference were individually and specifically indicated to be incorporated by reference and were set forth in its entirety.

What is claimed is:

1. An external ventilation system of a capsule pod sleeping chamber comprising:
    a wall of the capsule pod sleeping chamber, the wall including:
        an exterior side that faces a communal space; and
        an interior side that faces an interior of the capsule pod sleeping chamber;
    a duct to route first air out from the communal space to an area separated from air of the capsule pod sleeping chamber so as not to contaminate second air of the capsule pod sleeping chamber with the first air of the communal space, the duct being built into the wall, located between the exterior side and the interior side; and
    an aperture located on the exterior side opening into the duct.

2. The external ventilation system of claim 1, wherein the aperture is a vent with a mechanism for adjusting a flow rate of the first air through the vent.

3. The external ventilation system of claim 1, wherein the area separated from the air of the capsule pod sleeping chamber is occupied by a purifier unit.

4. The external ventilation system of claim 1, wherein the wall is composed of anti-microbial material.

5. The external ventilation system of claim 1, wherein the area separated from the air of the capsule pod sleeping chamber is external to the communal space.

6. The external ventilation system of claim 1, wherein the duct is configured to align and couple to an additional duct of an additional capture pod sleeping chamber located adjacent to the capsule pod sleeping chamber.

7. The external ventilation system of claim 6, wherein an entrance into the capsule pod sleeping chamber is located between the duct and the additional duct.

8. The external ventilation system of claim 1, further comprising:
    an additional duct to route third air into the communal space from a second area that is separated from the capsule pod sleeping chamber so as not to contaminate the first air of the communal space with the second air of the capsule pod sleeping chamber, the additional duct located between the exterior side and the interior side; and
    an additional aperture located on the exterior side that opens into the additional duct.

9. The external ventilation system of claim 8, wherein the additional duct is configured to align with one more duct of one more capsule pod sleeping chamber located adjacent to the capsule pod sleeping chamber.

10. The external ventilation system of claim 8, wherein the additional duct includes an ultraviolet light to disinfect the third air.

11. The external ventilation system of claim 8, wherein the additional duct includes a high-efficiency particulate air filter to remove particles from the third air.

* * * * *